United States Patent [19]

Becker

[11] Patent Number: 5,306,287
[45] Date of Patent: Apr. 26, 1994

[54] HEATED TISSUE FORCEPS AND METHOD

[76] Inventor: James H. Becker, P.O. Box 4835, Topeka, Kans. 66604

[21] Appl. No.: 969,064

[22] Filed: Oct. 30, 1992

[51] Int. Cl.⁵ .............................................. A61B 17/42
[52] U.S. Cl. ...................................... 606/205; 606/51; 606/52; 606/206; 606/207
[58] Field of Search .................... 219/227, 229; 604/20; 606/41, 42, 51, 52, 32, 205, 206, 207

[56] References Cited

U.S. PATENT DOCUMENTS

| | | | |
|---|---|---|---|
| 3,980,861 | 9/1976 | Fukunaga | 606/45 |
| 4,346,277 | 8/1982 | Wojtecki et al. | 219/528 |
| 4,715,273 | 12/1987 | Rieselmann | 99/382 |
| 4,883,942 | 11/1989 | Robak, Sr. et al. | 219/227 |

Primary Examiner—John D. Yasko
Assistant Examiner—Noelle Kent Gring
Attorney, Agent, or Firm—Hovey, Williams, Timmons & Collins

[57] ABSTRACT

Dissection forceps (10) include opposed arms (12) and (14), handle (16), cord (18), and power source adapter (20). Arms (12 and 14) are affixed with heating elements (68), (70) within body (56). Insulation (80, 82, 84, and 86), and insert (88) cooperate with elements (68, 70) in a manner that preferentially heats surfaces (30, 32) as well as points (26, 28). Forceps (10) are particularly useful in manipulating coated samples of biological tissues, such as samples that are encased in a layer of wax, because the heat prevents buildup of the coating substance upon arms (12 and 14) and, particularly, upon points (26 and 28).

2 Claims, 1 Drawing Sheet

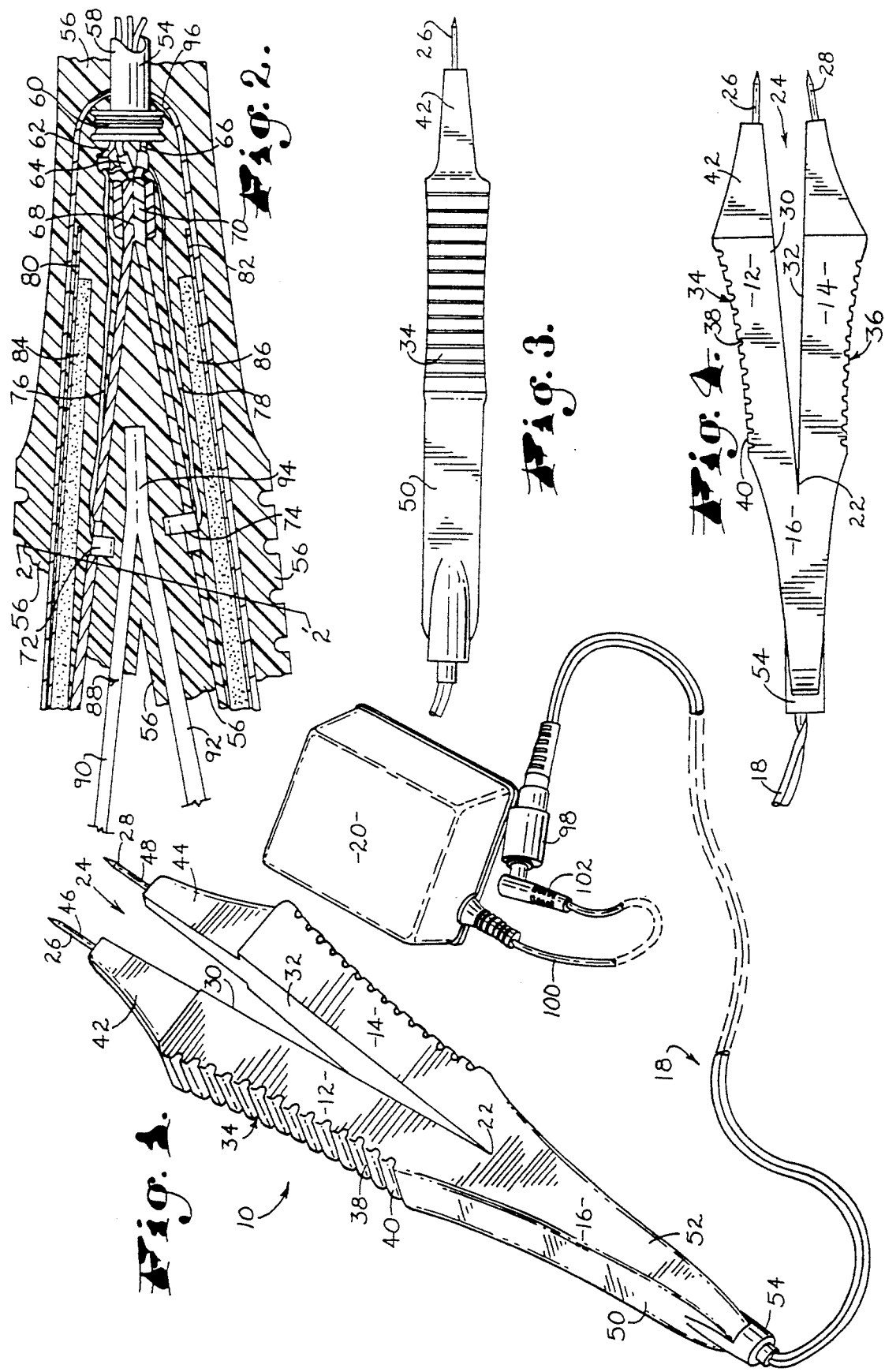

HEATED TISSUE FORCEPS AND METHOD

BACKGROUND OF THE INVENTION

1. Field of the Invention

The present invention broadly relates to forceps that are useful in the dissection and holding of biological tissue samples, and to a method for using the forceps to manipulate tissue samples having a chemical or wax substance that coats the outside of the sample. More particularly, the forceps of the invention include an opposed pair of coupled arms having structural means for manipulating tissue samples during the course of dissection studies. At least one of the arms is attached to means for electrically heating the arm with a sufficient quantity of heat to prevent an accumulation or buildup of the coating material upon the points of the forceps used for manipulating the samples. The method of using the forceps involves providing coated tissue samples, providing dissection forceps having affixed thereto means for electrical heating of the forceps, using power from an electrical source to heat the forceps to a temperature sufficient to melt the coating, and contacting the sample with the forceps.

2. Description of the Prior Art

Conventional tissue forceps are commercially available. Their structure is formed from a pair of thin metallic arms, wherein each arm is flexibly coupled at one end with the other arm, and each arm has a sharpened point extending from the non-coupled end. The method of their use includes flexing the opposed arms towards a central position in order to force the sharp points to come together and grasp small quantities of tissue or flesh.

One disadvantage of conventional forceps is that they do not work optimally well in certain dissection procedures wherein the tissues may be coated with viscous or solid substances. For example, in performing routine work such embedding macro-scale tissue samples within wax inside a cassette prior to insertion into a microtome for micro-scale shaving, a pathologist or technician must ordinarily manipulate the sample within hot wax. A wax buildup or accumulation on the forceps points typically interferes with the embedding procedure in a significant way.

The specific problem of wax buildup on dissection forceps has been addressed by devices such as heating wells. These devices generally have a box-like frame with hollow features connected to separate openings in which a number of conventional forceps may be placed for warming, removed for short term use until they have cooled and, subsequently, returned to the well for warming to a temperature that can melt wax. In general terms, the wells may be heated by electricity or by a bunsen burner. These heating wells have not fully solved the problem of wax buildup, however, because the cooled forceps must constantly be reheated since they have ceased to be effective against wax buildup.

SUMMARY OF THE INVENTION

The present invention resolves the problem of wax buildup on dissection forceps by providing a new type of tissue forceps wherein a heat source is affixed to the forceps themselves, not separately coupled with a heat well. In a broad sense, the dissection forceps of the invention comprise a pair of coupled arms having means for manipulating coated tissue samples during the course of dissection studies; means, affixed to at least one of the arms, for electrical heating thereof with sufficient heat for preventing the accumulation or buildup of the coat upon the means for manipulating the samples; and means for coupling the heating means with a source of electrical power.

More particularly, the arms each have respective pointed ends, and the arms are coupled together for opposed motion in a manner that allows the pointed ends to meet at a first position and move apart to a second position. Additionally, the electrical heating means is sufficient to prevent the accumulation of the coating material upon the pointed ends as the pointed ends contact the samples. Furthermore, the arms may be coupled together in a manner that allows movement between an open position where the arms are spaced apart, and a closed position where the arms meet together. The forceps may include a means for biasing the arms into the open position.

The forceps of the invention have numerous additional features that serve to enhance the utility of the forceps during dissection operations. The arms of the forceps have a flat heating surface that is capable of quickly removing excessive amounts of wax from a tissue sample that is being analyzed. The arms also have an insulated and textured gripping surface that can be grasped in order to move the arms of the forceps. The heating means of the invention may be an electrically resistive element such as an electric coil, or it can be an inductive heating element. The forceps arms may include a spring metal insert for biasing the arms apart, and this insert may have sharp prongs that protrude from the arms. The device may be operated from an alternating current power source, a direct current power source, or a portable source such as a battery.

The concept of the invention further offers a method of manipulating coated tissue samples. The method entails providing coated tissue samples, providing dissection forceps having affixed thereto means for the electrical heating of the forceps, using power from the source to heat the forceps to a temperature sufficient to melt the coating material, and contacting the sample with the forceps.

BRIEF DESCRIPTION OF THE DRAWINGS

FIG. 1 is a perspective view of the invention;

FIG. 2 is an enlarged fragmentation crossectional view of the forceps presenting various internal components of the forceps;

FIG. 3 is a side elevational view of the forceps; and

FIG. 4 is a front elevational view of the forceps.

DETAILED DESCRIPTION OF THE PREFERRED EMBODIMENT

Handheld tissue forceps 10, shown in FIG. 1, include arms 12 and 14, handle 16, electric cord 18, and electric adapter 20.

Arms 12 and 14 each have an elongated structure that starts at respective first ends, which begin at apex 22 of v-opening 24, and proceeds towards second ends that are defined by sharpened points 26 and 28. Flattened heating surfaces 30 and 32 exist along the sides of v-opening 24 opposite concave gripping surfaces 34 and 36 (FIGS. 1 and 4). Several peak and valley surface relief features, e.g., 38 and 40, provide gripping texture on surfaces 34 and 36. Wedge portions 42 and 44 taper along the longitudinal axis of arms 12 and 14 until points 26 and 28 begin (FIGS. 1, 3, and 4). Points 26 and 28 have respective flattened serrated edges 46 and 48.

Handle 16 forms a pyramidal structure having flattened sides, e.g., 50 and 52, that taper towards cord connector 54. FIG. 2 is a crossectional view that depicts the internal components of handle 16 as well as a similar partial crossectional view of arms 12 and 14. Flexible latex body 56 forms a main body wherein various other components (58 through 94) are hidden from the exterior perspective. Connector 54 includes a tubular portion 58 and a concentric wire retaining plug 60 of larger radial diameter through which extend wires 62, 64, and 66. Wires 64 and 66 are divided positive leads that extend from a common positive lead within cord 18, and they clip-connect to respective heating elements 68 and 70. Anti-rotation clips 72 and 74 attach to respective heating elements 68 and 70, wherefrom ground lines 76 and 78 extend towards ground wire 62. Foil heat shields 80, 82 extend along the length of arms 12 and 14 and also partially within handle 16. Those are in proximal relation to foam insulation heat barriers 84 and 86 which similarly extend along the length of arms 12 and 14. Spring metal insert 88 is formed of two legs 90 and 92, which are joined together at welded portion 94. Insert 88 is entirely encased within body 56, with the exception of points 26 and 28 which protrude from the body. Boot 96 forms a U-shaped structure that generally contains the internal components 58 to 94. Thus, the line along 2-2' (FIG. 2) contacts body 56, boot 96, foil heat shield 82, heat barrier 86, body 56, heating element 70, body 56, leg 92, body 56, leg 90, body 56, heating element 68, body 56, heat barrier 84, body 56, shield 80, boot 96, and body 56.

Heating elements 68 and 70 most preferably operate on the principle of electrical resistance for the purpose of producing heat. Various types of resistive heat producing elements are known in the art, but the most preferred types are those having a coiled heating element. Of course, other types of heating elements, such as inductive elements, are known and may also be adapted for practice in the invention.

Cord 18 contains wires 62, 64 and 66, which travel to female adapter plug connection 98. Again, note that wires 64 and 66 represent branches from a common or single positive lead within cord 18. Adapter 20 is most preferably an adapter of the type that converts alternating current ("AC") from a standard dual prong one-hundred and twenty volt electrical wall plug outlet into direct current ("DC"). While the dual prongs of adapter 20 are not depicted, many such devices are commercially available, and one such example is the Uniden Model AD-140U which is of Taiwanese construction and converts an AC signal at 120 volts, 60 Hz, and 14 watts to a DC output of 500 mA. Adapter 20 includes adapter wire 100, which carries positive and negative leads (not depicted) to male adapter plug 102.

In operation, adapter 20 is plugged into a standard household wall electrical outlet, and it begins converting AC into DC. The current travels along positive leads 64 and 66 within cord 18, through heating elements 68 and 70, and through ground lines or wires 76, 78, and 62. The current heats elements 68 and 70 which, in turn, transfer heat to body 56 as well as elements elements 58, 60, 62, 64, 66, 68, 70, 72, 74, 76, 78, 80, 82, 84, 86, 88, 90, 92, 94, and 96, therein. Eventually, the heat raises the temperature in portions of arms 12 and 14 to that which is at least sufficient to melt the wax which is utilized and, most preferably, at least one-hundred forty degrees fahrenheit (140° F.). The quantity of heat transfer to heating surfaces 30 and 32 is greater than the heat transfer to gripping surfaces 34 and 36, because heat barriers 84 and 86 cooperate with foil heat shield 80 to block heat transfer towards surfaces 34 and 36. Thus, surfaces 30 and 32 are relatively hot and generally capable of melting wax, while surfaces 34 and 36 provide a comfortable grip for a forceps user. Furthermore, body 56 conducts this focused heat energy into metallic insert 88, which ultimately transfers the heat to points 26 and 28 where the temperature rises to a level that itself can melt wax, or at least prevent the accumulation or buildup of wax upon points 26 and 28 of arms 12 and 14.

Arms 12 and 14 are flexibly coupled by means of latex body 56 and also insert 88. In particular, insert 98 helps to configure arms 12 and 14 for the purpose of manipulating flesh during the course of a dissection analysis because the spring legs 90 and 92 flex inwardly towards v-opening 24 as a forceps user applies pressure to gripping surfaces 34 and 36. Legs 90 and 92 bend inwardly until points 26 and 28 come together in a closed position where it is possible to grasp biological tissues for analysis between the points. When the forceps user releases surfaces 34 and 36, legs 90 and 92 serve to bias arms 12 and 14 into an open position as is depicted in FIGS. 1 and 4.

The forceps are generally useful tools in practicing a general method of manipulating coated tissue samples. The method entails providing coated tissue samples, providing dissection forceps having affixed thereto means for electrically heating the forceps (e.g., elements 68, 70), using power from an electrical power source to heat the forceps to a temperature sufficient to melt the coating material, and contacting said sample with said forceps.

By way of particular example, a pathologist may wish to insert a tissue sample from a biopsy procedure into a cassette which contains liquid wax in order to embed the sample in wax for cutting in a microtome. These samples might range in size from about the size of a pinhead to about the size of the cassette which, for example, may form a square cube having sides of about one inch in length. The pathologist may easily grasp a tiny sample for manipulation with points 26 and 28, and the heat therefrom will preclude waxy buildup on the points. In other applications where a sample may be surrounded by excessive amounts of wax, or may require thawing, the sample can be rapidly heated by placing it within V-opening 24 and contacting it with surfaces 30 and 32.

It should be understood that the description herein is that of the preferred embodiment. Those who are skilled in the art will recognize that other, less preferred, embodiments exist that may still allow one to practice the invention. By way of example, adapter 20 might also be a simple electrical plug for conducting alternating current for a heating element that is configured to so operate. Alternatively, the power source could be a battery pack. Points 26 and 28 may be of a type that detachably connect to insert 88, which may be made of polymer or other flexible material. Surfaces 30 and 32 may be rounded instead of flat. Arms 12 and 14 might be pivotally connected instead of flexibly attached. These types of rearrangements and substitutions may be made without departing from the spirit and the scope of the invention.

I claim:

1. Dissection forceps comprising:

a pair of elongated arms, each of said arms respectively having a first end, a second end, and a midsection, said midsection having a heatable surface and an insulated surface positioned along the length of said arms;

a flexible coupling between said respective first ends, which allows said second ends a limited range of opposed motion as said arms come together and move apart;

a spring insert positioned within said arms to bias said arms into a position a fixed distance apart, said insert having sharp prongs that protrude from within said arms;

an electronic heat source element forming a part of the structure of said one of said arms; and means for coupling said heat source element with a source of electric power, each of said arms having a layered crossectional construction including a flexible body, said metal insert, said body, said element, said body, foam insulation, a foil heat shield, and said body.

2. A method of manipulating coated tissue samples, comprising:

providing coated tissue samples;

providing dissection forceps having affixed thereto means for the electrical heating of said forceps;

using power from an electrical power source to heat said forceps to a temperature sufficient to melt said coating; and contacting said sample with said forceps.

* * * * *